(12) United States Patent
Robertson

(10) Patent No.: US 9,880,354 B2
(45) Date of Patent: Jan. 30, 2018

(54) SURFACE ELECTROMAGNETIC WAVES IN PHOTONIC BAND GAP MULTILAYERS

(71) Applicant: William M. Robertson, Goodlettsville, TN (US)

(72) Inventor: William M. Robertson, Goodlettsville, TN (US)

( * ) Notice: Subject to any disclaimer, the term of this patent is extended or adjusted under 35 U.S.C. 154(b) by 0 days.

(21) Appl. No.: 14/962,861

(22) Filed: Dec. 8, 2015

(65) Prior Publication Data

US 2016/0223747 A1 Aug. 4, 2016

Related U.S. Application Data

(63) Continuation of application No. 14/244,961, filed on Apr. 4, 2014, now Pat. No. 9,207,358, which is a continuation of application No. 13/424,449, filed on Mar. 20, 2012, now Pat. No. 8,692,211.

(60) Provisional application No. 61/454,569, filed on Mar. 20, 2011.

(51) Int. Cl.
| | |
|---|---|
| *G01N 21/64* | (2006.01) |
| *G02B 6/122* | (2006.01) |
| *G02B 1/00* | (2006.01) |
| *B82Y 20/00* | (2011.01) |
| *G01N 21/552* | (2014.01) |
| *G02B 6/124* | (2006.01) |
| *G02B 6/136* | (2006.01) |
| *G02B 6/293* | (2006.01) |
| *G02B 6/34* | (2006.01) |

(52) U.S. Cl.
CPC ............ *G02B 6/1225* (2013.01); *B82Y 20/00* (2013.01); *G01N 21/553* (2013.01); *G01N 21/648* (2013.01); *G01N 21/6428* (2013.01); *G01N 21/6486* (2013.01); *G02B 1/005* (2013.01); *G02B 6/124* (2013.01); *G02B 6/1226* (2013.01); *G02B 6/136* (2013.01); *G02B 6/2934* (2013.01); *G02B 6/34* (2013.01)

(58) Field of Classification Search
CPC .................................................... G01N 21/553
See application file for complete search history.

(56) References Cited

U.S. PATENT DOCUMENTS

2004/0008437 A1* 1/2004 Kittaka .................. B82Y 20/00
359/883

OTHER PUBLICATIONS

Mir et al., "Large omnidirectional band gaps and selective transmission in one-dimensional multilayer photonic structures," 2001, Vacuum, vol. 63, pp. 197-203.*
Shinn et al., "Surface plasmon-line sensor based on surface electromagnetic waves in a photonic band-gap material," 2005, Sensors and Actuators B, vol. 105, pp. 360-364.*

* cited by examiner

*Primary Examiner* — Kiho Kim
(74) *Attorney, Agent, or Firm* — Wayne Edward Ramage; Baker Donelson

(57) ABSTRACT

A device and associated methods for using surface electromagnetic waves (SEWs) generated at the surface of photonic band gap multilayers (PBGMs) in place of surface plasmons (SPs) in metal films. One device is a photonic circuit comprising a multilayer apparatus to generate surface electromagnetic waves, wherein the surface electromagnetic waves comprise the signal medium within the circuit. The circuit may be formed or etched on the surface of the multilayer apparatus.

7 Claims, 7 Drawing Sheets

Enhanced fluorescent detection from microarrays utilizing prism coupled illumination to generate SEWs and imaging of the resulting fluorescence from the array elements.

Kretschmann prism coupling configuration for a dielectric multilayer (SEWs)

Plot of reflectivity versus angle for surface plasmon coupling (red curve) and for SEW coupling (blue curve).

Plots of electromagnetic field enhancement ($|E|^2$ relative to $E=1$ in the prism) for (a) Surface plasmon and (b) and (c) two different photonic band gap multilayers.

Enhanced fluorescent detection from microarrays utilizing prism coupled illumination to generate SEWs and imaging of the resulting fluorescence from the array elements.

Propagation distance of a surface electromagnetic wave on a multilayer (upper plot) and a surface plasmon on a silver film (lower plot)

Schematic outline of a SEW photonic circuit formed by lithographic etching into the top surface of a PBGM Three schemes for SEW localization in the surface of a PBGM. (a) Defect in 2-dimensional band gap array. (b) Defect in a Bragg grating structure (c) Annular ring resonator

SURFACE ELECTROMAGNETIC WAVES IN PHOTONIC BAND GAP MULTILAYERS

This application is a continuation of U.S. patent application Ser. No. 14/244,961, filed Apr. 4, 2014, now issued as U.S. Pat. No. 9,207,358, issued Dec. 8, 2015, by William Robertson, which is a continuation of U.S. patent application Ser. No. 13/424,449, filed Mar. 20, 2012, now issued as U.S. Pat. No. 8,692,211, issued Apr. 8, 2014, by William Robertson, which claims benefit of and priority to U.S. Provisional Application No. 61/454,569, filed Mar. 20, 2011, by William Robertson, and is entitled to those filing dates for priority. The specification, figures and complete disclosure of U.S. patent application Ser. Nos. 14/244,961 and 13/424,449, and U.S. Provisional Application No. 61/454,569, are incorporated herein by specific reference for all purposes.

FIELD OF INVENTION

The invention disclosed herein involves optical sensing configurations designed to detect trace amounts of biological and chemical entities or as components in photonic circuits or telecommunications and optical computing applications, as well as methods for utilizing these configurations.

BACKGROUND OF THE INVENTION

The use of surface plasmon sensors is well known in the prior art. Surface plasmons are used in a variety of applications, most notably in biological and chemical sensors, based on the perturbation of surface plasmon resonance by dielectric loading. Surface plasmon sensors are a class of sensors with a long and commercially successful history. They are principally used to detect small amounts of biological entities. The active element of a surface plasmon sensor is a metal film. In a typical surface plasmon sensor the metal surface is prepared with an antibody to a particular protein bound to the metal surface. The angle of surface plasmon coupling is determined and then the film is exposed (usually by the use of a flow cell) to a sample that is being tested for the targeted protein. If the protein is present in the sample solution it binds to the antibody, adding a dielectric-loading layer to the metal surface. This extra layer leads to an alteration in the angle of surface plasmon coupling, thus indicating the presence of the protein. The metal film thickness is typically about one tenth of the wavelength of the incident light. At angles of incidence, θ, greater than the angle for total-internal reflection, the light creates an evanescent field that can penetrate through the metal. Surface plasmons are resonantly generated at the angle of incidence at which the wave vector and frequency of the evanescent field match those of surface plasmons at the metal-air interface. The most obvious manifestation of this coupling is a drop in the intensity of the reflected light.

In practice, surface plasmon sensors have some limitations. Because of its sharp resonance, silver would appear to be the best material for making sensors with high surface sensitivity. However, because silver is chemically reactive it is not suitable in most applications. Similar reactivity issues eliminate copper and aluminum. Gold is thus the standard material for essentially all commercially available surface plasmon sensors. However, gold has a less well-defined resonance than silver because of its higher dielectric loss. Gold films have limited sensitivity to dielectric changes at the surface because of the difficulty of accurately detecting small angle shifts of the broad resonance. Furthermore, the optical properties of gold mean that it only supports surface plasmons at longer wavelengths in the red and infrared.

Surface plasmons have been similarly proposed for a variety of other (currently less commercial) applications in which their enhanced surface electromagnetic fields are used to amplify linear or non-linear optical processes, their sub-wavelength optical character is used for imaging or lithography, and the propagating surface plasmon is used to create a compact photonic circuit to perform manipulation of electromagnetic wave signals. Similar disadvantages, such as the relatively short propagation distance of a surface plasmon, apply to these applications as well.

SUMMARY OF INVENTION

In various embodiments, the present invention provides for an optical multilayer structure constructed so as to cause the structure to exhibit a photonic band gap. In one exemplary embodiment, the structure comprises an optical multilayer deposited or disposed on an optically transparent substrate or side of a prism, the optical multilayer being formed of a series of alternative layers of high refractive index materials and low refractive index materials. The thickness of the layers is selected so as to cause the structure to exhibit a photonic band gap. A terminating layer deposited on the multilayer such that a surface optical mode exists at a wavelength within the photonic band gap.

The photonic band gap apparatus may then be used in a variety of devices. In one embodiment, the device is a photonic circuit comprising a multilayer apparatus to generate surface electromagnetic waves, wherein the surface electromagnetic waves comprise the signal medium within the circuit. The multilayer apparatus comprises a prism with an optical dielectric multilayer deposited on one side.

DETAILED DESCRIPTION OF EXEMPLARY EMBODIMENTS

Figure 1:
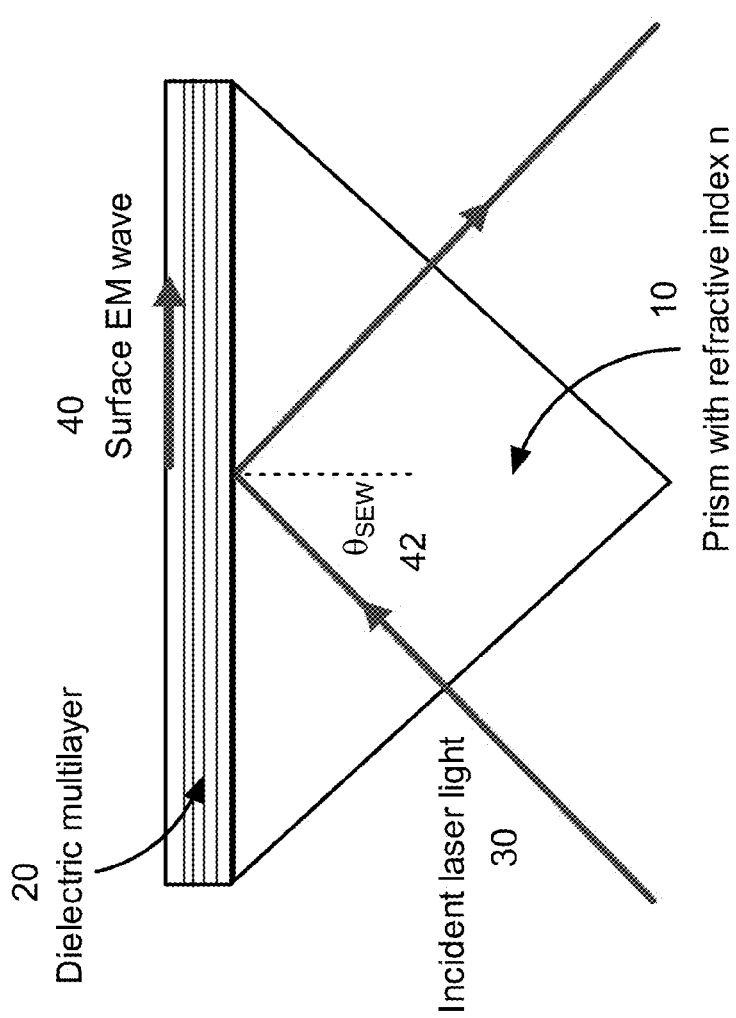
FIG. 1 shows a prism configuration used to generate surface electromagnetic waves in accordance with an exemplary embodiment of the present invention.

In various embodiments, the present invention comprises devices and associated methods for using surface electromagnetic waves (SEWs) generated at the surface of photonic band gap multilayers (PBGMs) in place of surface plasmons (SPs) in metal films. The general use and construction of an optical multilayer structure constructed so as to cause the structure to exhibit a photonic band gap is described in U.S. patent application Ser. Nos. 12/207,866; 12/047,978; and 11/468,343; the complete disclosures of which are incorporated herein in their entireties by specific reference for all purposes.

SEWs are electromagnetic (EM) modes that propagate at the interface between a passive dielectric material and a so-called active medium (i.e., one whose real part of the dielectric function is less than −1 at the frequency of interest). The dispersion of SEWs is such that they are non-radiative, which means that they do not couple directly to light. Excitation of surface EM modes requires the use of a prism or a grating configuration in order to phase match incident light to the surface mode and facilitate resonant coupling between light and the surface EM modes.

The most widely studied type of surface electromagnetic waves are those that exist at the surfaces of metals. These modes are known as surface plasmons. A number of metals exhibit a sufficiently negative real part of the dielectric function so as to support surface plasmons; however, most metals also have strong dielectric loss (i.e., the large imaginary part of the dielectric function), which means that the resonant excitation of surface plasmons is heavily damped. In practice, there are a handful of metals with low loss that exhibit pronounced surface plasmon effects—e.g., silver, gold, copper, and aluminum. Silver and aluminum are the best across wavelengths in the visible range. Gold and copper show good surface plasmon effects in the red and infrared range.

PBGMs are periodic composites that can be engineered to exhibit metal-like optical properties over given frequency intervals. A PBGM is composed of two constituents with different dielectric constants arranged with a regular periodicity in one, two, or three dimensions. The coherent effects of scattering and interference result in a dramatic modification of the dispersion relation for light traveling in the composite, including the appearance of photonic band gaps—frequency intervals in which the propagation of light is forbidden. In the forbidden transmission regions, the PBGM has metal-like behavior and the optical response of the composite can be described by an effective dielectric constant with a negative real value. It is this negative effective dielectric constant that permits the material to support SEWs at frequencies within the forbidden transmission band.

SEWs in PBGMs have some distinct advantages over surface plasmons. For sensing applications there are two differences that are particularly important. First, the dielectric loss in PBGMs is determined by the loss of the constituent materials and it is typically orders of magnitude lower than the dielectric loss of even the best surface plasmon active metals. Low dielectric loss translates into very sharp SEW resonance excitation and concomitantly enhanced sensitivity. Although the question of sensor performance is complex, in simple terms PBG-based sensors can be orders of magnitude more sensitive than surface plasmon sensors. Second, the response of the one-dimensional PBG material can be engineered so that surface waves can be generated at any wavelength. In contrast, for surface plasmon phenomena the dielectric properties of the metal determine the wavelength range of operation. For example, gold, the most commonly used surface plasmon sensing material, is limited to wavelengths in the red and infrared.

SEWs in PBGMs, as described herein, can be used in a variety of applications, including, but not limited to, biological and chemical sensors, amplification of linear or non-linear optical processes, imaging or lithography, and the manipulation of electromagnetic wave signals. The use of SEWs in PBGMs in place of surface plasmons provides several advantages, including, but not limited to, much lower dielectric loss in PBGMs than in the metal films used to generate surface plasmons. This difference in loss leads to a much sharper optical coupling resonance, as demonstrated graphically in FIGS. 1 and 2.

FIG. 1 shows an example of a prism configuration used to generate SEWs using a dielectric multilayer apparatus (i.e., a prism 10 with a multilayer 20 formed on one side). Collimated laser light 30 incident through the prism 10 couples to surface waves 40 when the angle of incidence 42 is such to permit phase matching to the appropriate surface wave mode.

Figure 2:
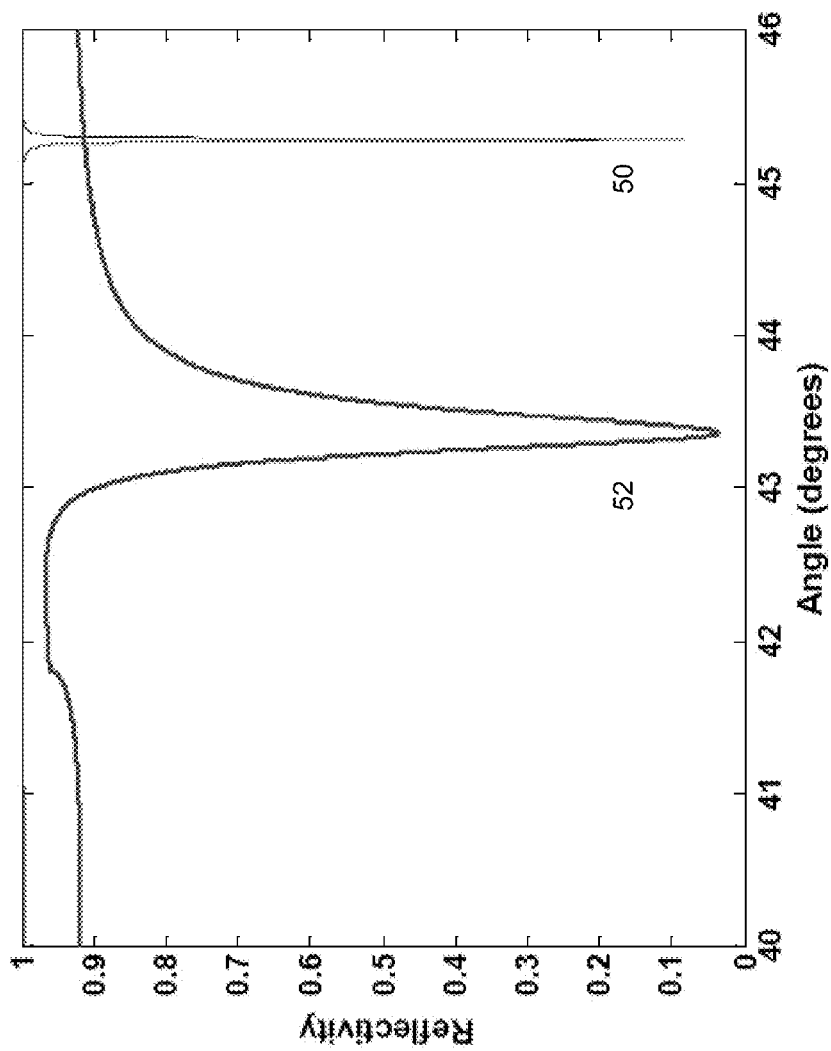
FIG. 2 shows a comparative plot of reflectivity versus angle for surface plasmon coupling (left curve) and for surface electromagnetic wave coupling (right curve).

FIG. 2 shows a comparison of the result of coupling on the reflected light between the SEW apparatus of FIG. 1 as compared to an apparatus using a metal film to generate surface plasmons. At the resonant coupling angle, there is a sharp drop in reflected light because the energy is being channeled into the surface wave. However, it is clear that the optical coupling resonance width is much narrower in the case of SEWs 50 in PBGMs (right curve) than in the case of surface plasmon coupling 52 (left curve).

The sharper resonant coupling is indicative of the much lower dielectric loss in the case of the PBGM compared to the metal film. The lower loss also means that the resonant enhancement of the incident optical field of SEWs in PBGMs experiences a greater enhancement than for surface plasmons in metal films.

Figure 3:
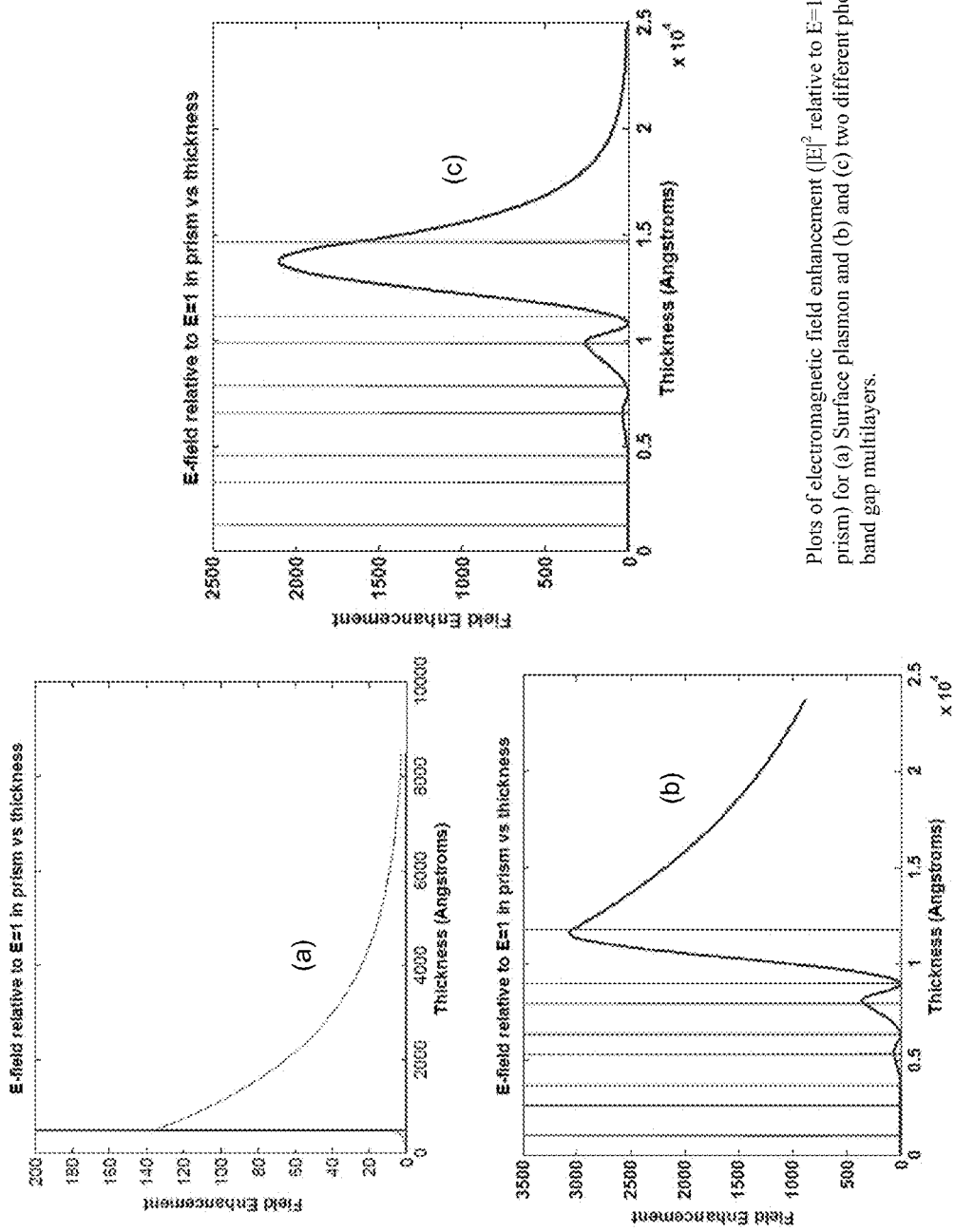
FIG. 3 shows comparative plots of electromagnetic field enhancement for surface plasmon and two different photonic band gap multilayers.

This difference in surface field enhancement is demonstrated in FIG. 3. The top panel shows the field intensity enhancement for surface plasmon generation. The plot shows that the field intensity ($|E|^2$) at the metal surface (vertical red line at 500 Angstroms) is enhanced by about 140 times compared to the incident field of the light (E=1). Panels 2 and 3 of FIG. 3 show that the surface field intensity of the SEWs generated in a PBGM is enhanced by between 1500 and 3000 times. Stronger field amplification means that linear and non-linear optical phenomena (e.g., molecular fluorescence (linear) or Raman scattering (non-linear)) would experience a much larger enhancement in the PBGM case than in the metal film case. Furthermore panels 2 and 3 demonstrate that the field penetration depth beyond the surface of the PBGM can be tailored by the design of the period and termination layer of the PB GM. The field in panel 2 extends considerably further than that in panel 3.

One application of the enhanced surface field intensity of SEWs is for an enhanced sensitivity microarray reader using in biological sensing of protein and DNA binding. The typical means of reading microarrays is through the use of probe hybridization to DNA or antibody binding with protein. Probes or antibodies are modified by the addition of a fluorophore. Current array reading devices operate to detect binding by illuminating the array with a wavelength that excites fluorescence from the fluorophore. The fluorescent signal from the array is imaged onto a CCD camera to identify the array spots where binding has occurred. The limitation in this process is that there must be sufficient fluorescent signal, and hence sufficient number of bound fluorescent probes, to reliably detect binding. The enhanced electromagnetic fields associated with SEW generation can be used to increase the effective illumination of the bound fluorophores (theoretically by up to a factor of 4000 times) and thus increase their fluorescent yield. Increased yield would enable sensing of smaller quantities of bound fluorophores effective increasing the sensitivity of array readers. The PBG multilayers can be designed to produce a SEW that will work with the most common fluorophores used currently Cy5 (excitation 649 nm, emission 670 nm) and Cy3 (excitation 550 nm, emission 570 nm).

Figure 4:
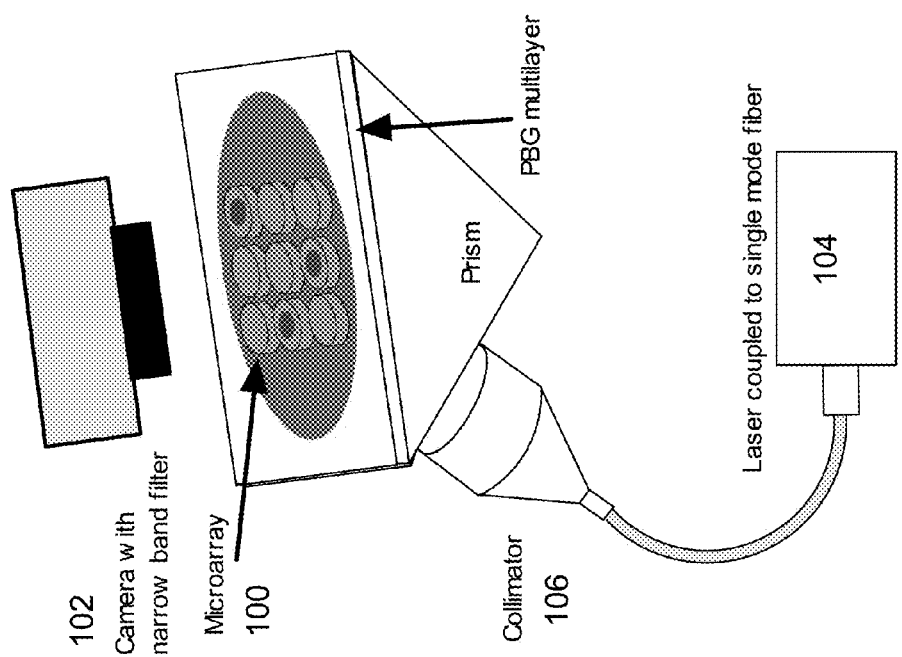
FIG. 4 shows a method for enhanced fluorescent detection from microarrays utilizing prism-coupled illumination to generate SEWs.

One embodiment of a device the makes use of the elevated surface electromagnetic fields associated with SEW generation is shown in FIG. 4. The configuration uses a large collimated beam to illuminate an entire microarray 100. The fluorescence from the array is measured by imaging the entire array onto a low noise CCD camera 102. A filter excludes any of the scattered laser light. A key design factor is the requirement to prism couple a high fraction of the incident light into SEWs. To accomplish strong conversion the incident light needs to be at the correct coupling angle. For surface plasmons this condition is not difficult to fulfill because the angular width of the resonance is of the order of 1° or more. In contrast, the SEW resonance has an angular width of about 0.05°. The difference in angular coupling width is evident from FIG. 2. To get a large fraction of the light coupled into the SEW mode the incident light in the device shown in FIG. 4 is made parallel by using the laser output of a single mode fiber optic 104 and a large diameter collimator 106.

The lower dielectric loss also means that the SEWs travel much further along the surface of the PBGM sample than surface plasmons travel in metal films. There has been some discussion of using surface plasmons to create photonic circuits. The rationale is that the surface plasmon is an optical excitation that is sub-wavelength (i.e., it is shorter than light of the same frequency) so that such circuits could be compact. However, as most proponents point out, the propagation distance of a surface plasmon is only between 10 and 100 μm, thereby making complicated or extended circuits impractical.

Figure 5:
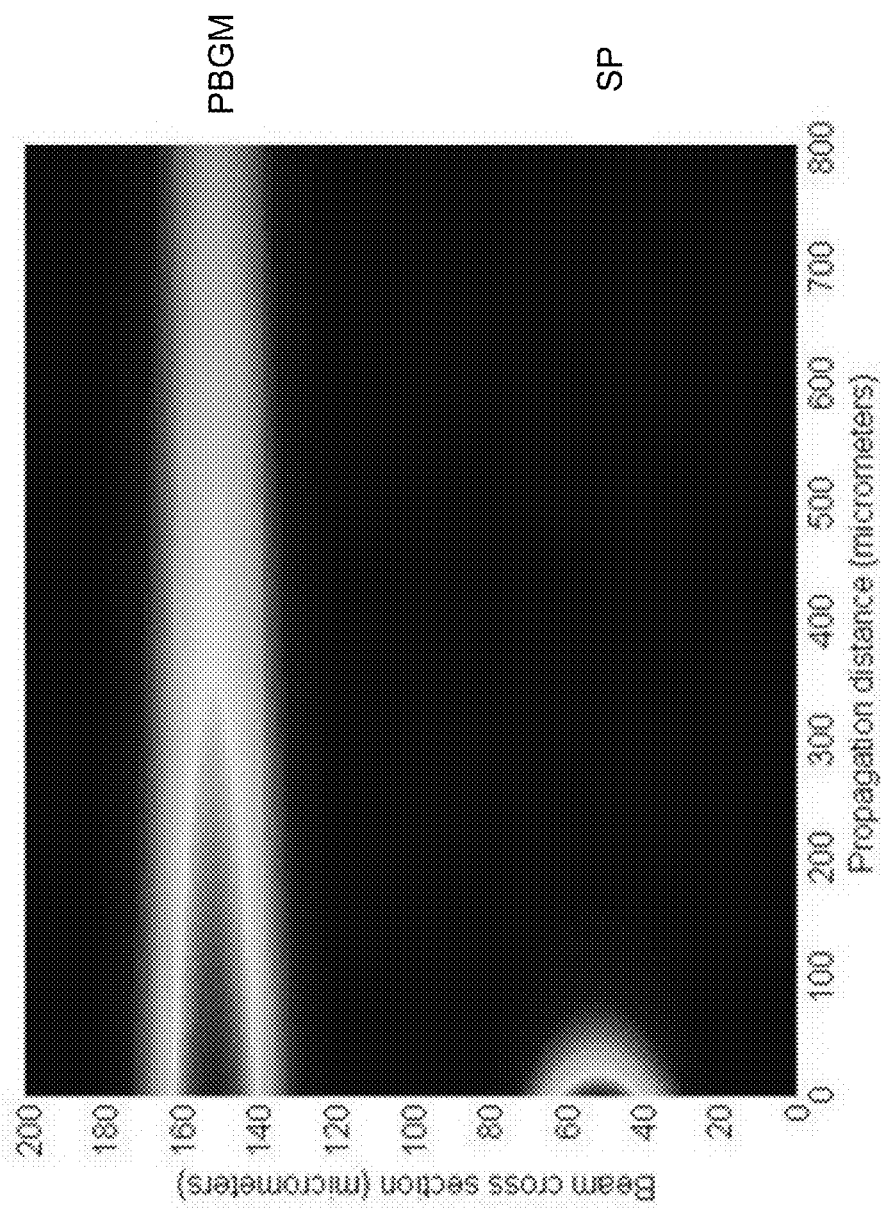
FIG. 5 shows a comparative plot of the propagation distance of surface plasmons on a silver film and SEWs on a photonic band gap multilayer.

In contrast, the SEWs in PBGMs propagate about 100 times further than surface plasmons (i.e., 100 to 1000 μm), making even elaborate circuits possible. This difference in propagation distance is demonstrated in FIG. 5. This figure shows the calculated propagation distance for SEWs in a PBGM (upper curve) versus a surface plasmon in a silver film (lower plot). Furthermore, the wavelength of the SEW can be manipulated by the PBGM design to be shorter than the shortest surface plasmon wavelength. Accordingly, compact photonic circuits using SEWs in PBGMs can be created effectively.

Figure 6:
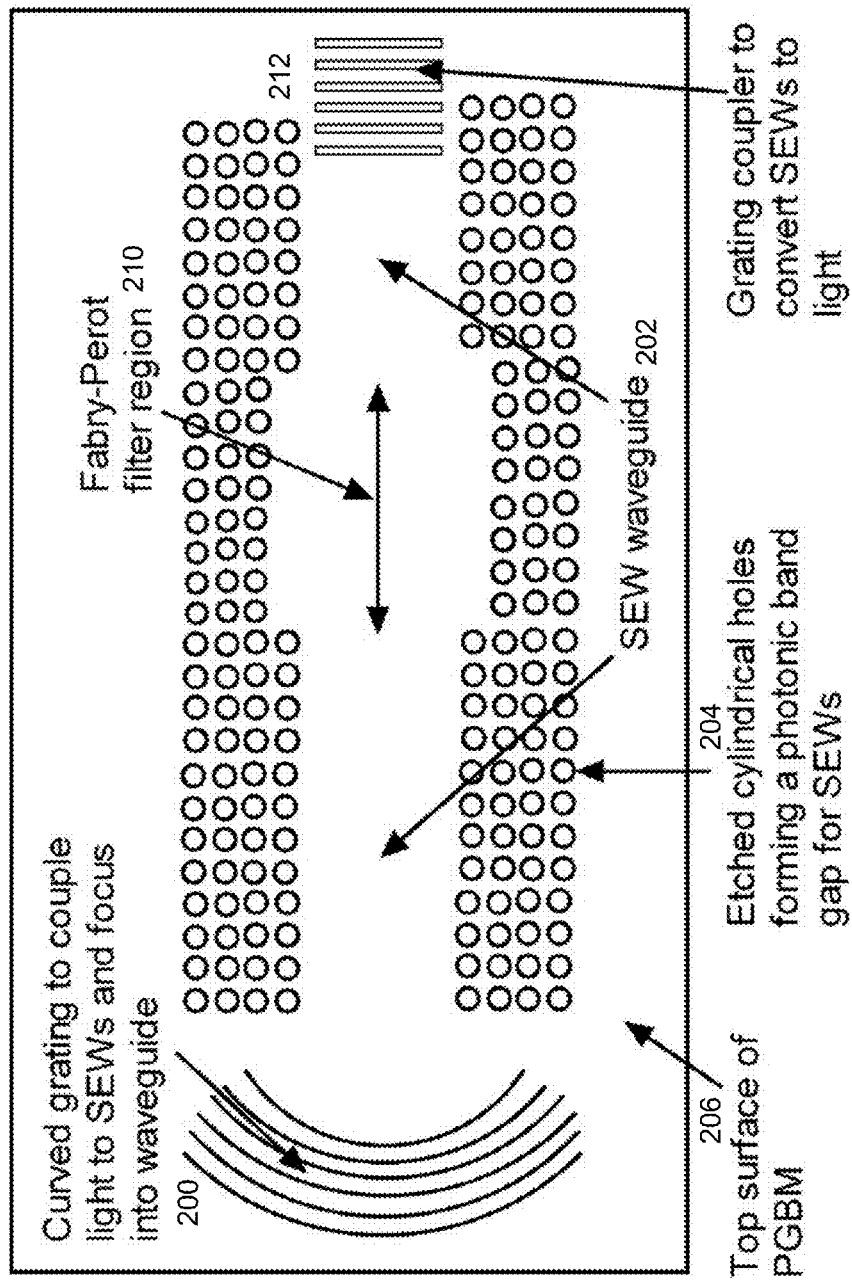
FIG. 6 shows a schematic outline of a photonic circuit based on control and direction of SEWs propagating at the surface of a PBGM.

There has been growing interest in using modified metal surfaces designed to direct and control the flow of surface plasmons in order to form circuits capable of operating on optical signals. The aim is to produce a technology that combines the broad bandwidth of photonics with the compactness of electrical circuitry. A major drawback of using surface plasmons is their short propagation distance. This problem is obviated by the use of much longer propagation distance SEWs on PBGMs. The enabling methods employed for surface plasmon circuitry that has been used to create couplers, waveguides, lenses, mirrors, interferometers, can be implemented for SEWs on PGBMs. The techniques of creating elements that direct and control the flow of SEWs typically involve etching or spatially modifying the index of the top surface of a PBGM in order to create structures such as gratings, lenses, or hole arrays that form SEW band gaps structures. FIG. 6 illustrates schematically a simple SEW circuit structure. The leftmost element is a curved grating structure 200 designed to couple a laser spot into SEWs in the surface as well as focusing the resulting SEWs into the end of a waveguide 202. The waveguide walls are formed by a photonic band gap array consisting of periodically-spaced holes 204 etched into the top surface of the PBGM 206. A Fabry-Perot etalon 210 is formed by expanding the waveguide width over a short interval. Finally, a grating structure 212 couples the filtered SEWs back into an optical signal.

Although the long propagation distance of SEWs is desirable for creating photonic circuits there is a second class of surface modification that seeks to frustrate the long propagation distance to create a spatially confined SEW excitation of a PBGM. Localizing the SEW mode in the plane of excitation serves two purposes. First, the localized resonance can be used for label-free sensing from small areas of the PBGM. Second, the confinement could be used to create substantially greater enhancement of linear or non-linear optical phenomena. Localization enhances the already high surface electromagnetic fields of the SEWs by further confining their propagation. This approach is motivated by noting that the highest plasmonic enhancement phenomena—such as that for surface enhanced Raman Scattering—are associated with surface plasmons localized in small metal particles or surface features.

Figure 7:
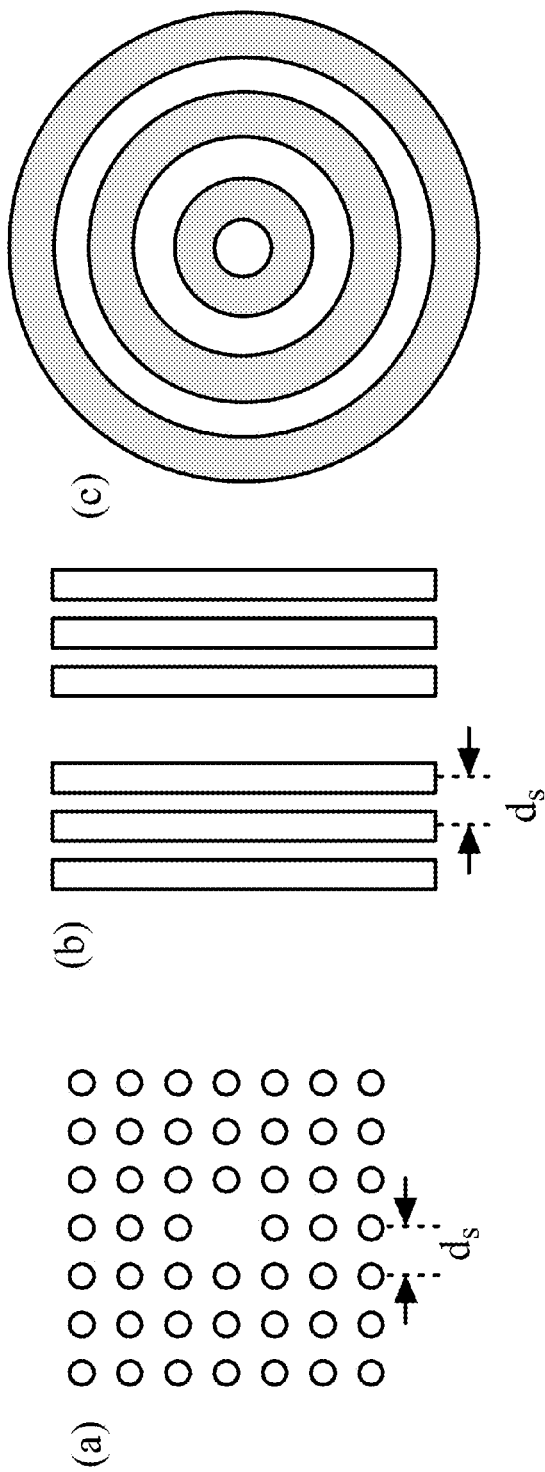
FIG. 7 shows three schemes for creating a SEW excitation that is spatially localized within the plane of the PBGM.

Three potential localization schemes are illustrated in FIG. 7. In the first (FIG. 7(a)) the periodic indentation array creates an in-plane band gap for the SEWs. The missing element in the center of the regular array acts as a resonant defect state within the forbidden band gap. FIG. 7(b) shows a similar arrangement but with confinement only along one direction. Finally, FIG. 7(c) shows an annular ring resonant structure. The key in the design of these surface elements is to select the periodicity $d_s$ in such a manner that the SEWs are not grating coupled into light and hence radiatively damped.

Because of the dramatically lower dielectric loss factor, SEWs in PBGMs have narrower optical coupling resonances, higher surface field enhancements, and much longer propagation lengths than surface plasmons in metal films. These factors can lead to significant advantages in sensing (narrower resonance width), enhancement of linear and non-linear optical effects (higher surface fields), and photonic circuits (longer propagation distance). SEWs in PBGMs are also of advantage because the properties of the optical response of the multilayer can be tailored to the application at hand by the appropriate choice of the periodicity and the termination layer. SEWs can be generated at any wavelength whereas surface plasmons depend on the fixed characteristics of existing metals. Unlike surface plasmons in metal films, the wavelength of the SEW at a given optical frequency can be adjusted over a significant range, and the field penetration into the space beyond the multilayer can be engineered by the design of the PBGM.

Thus, it should be understood that the embodiments and examples described herein have been chosen and described in order to best illustrate the principles of the invention and its practical applications to thereby enable one of ordinary skill in the art to best utilize the invention in various embodiments and with various modifications as are suited for particular uses contemplated. Even though specific embodiments of this invention have been described, they are not to be taken as exhaustive. There are several variations that will be apparent to those skilled in the art.

What is claimed is:
1. An apparatus, comprising:
  a photonic band gap multilayer structure comprising a series of alternating layers of high refractive index materials and low refractive index materials, said multilayer structure with a top surface, wherein the multilayer structure generates surface electromagnetic waves on the top surface; and a photonic circuit formed in or on the top surface of the multilayer structure, wherein the surface electromagnetic waves comprise a signal medium within the photonic circuit, said photonic circuit comprising an annular ring resonator;

further wherein the surface electromagnetic waves are spatially confined by said annular ring resonator.

2. The apparatus of claim 1, wherein the photonic circuit is a photonic integrated circuit.

3. The apparatus of claim 1, wherein the multilayer structure is a dielectric multilayer.

4. The apparatus of claim 1, wherein the photonic circuit is etched into the top surface.

5. The apparatus of claim 1, wherein the photonic circuit comprises a focus to guide surface electromagnetic waves into the annular ring resonator.

6. The apparatus of claim 1, wherein the photonic circuit comprises a conversion grating to convert the surface electromagnetic waves to an optical signal.

7. A method for constructing a photonic circuit, comprising the steps of:
providing a surface electronic wave waveguide comprising an annular ring resonator on a top surface of a photonic band gap multilayer structure;
coupling light from a source to surface electromagnetic waves on the top surface of the photonic band gap multilayer structure, said structure comprising a series of alternating layers of high refractive index materials and low refractive index materials;
focusing the surface electromagnetic waves into a surface electromagnetic wave waveguide; and
converting the surface electromagnetic waves into an optical signal.

* * * * *